(12) United States Patent
Fisch et al.

(10) Patent No.: US 6,781,687 B2
(45) Date of Patent: Aug. 24, 2004

(54) ILLUMINATION AND IMAGE ACQUISITION SYSTEM

(75) Inventors: David Fisch, Paduelle (IL); Yigal Katzir, Rishon Lezion (IL)

(73) Assignee: Orbotech Ltd., Yavne (IL)

( * ) Notice: Subject to any disclaimer, the term of this patent is extended or adjusted under 35 U.S.C. 154(b) by 0 days.

(21) Appl. No.: 10/254,542

(22) Filed: Sep. 26, 2002

(65) Prior Publication Data

US 2004/0061850 A1 Apr. 1, 2004

(51) Int. Cl.[7] .............................................. G01N 21/00
(52) U.S. Cl. ................................................... 356/237.2
(58) Field of Search ........................ 356/237.1–237.4; 250/562, 572; 382/141, 151

(56) References Cited

U.S. PATENT DOCUMENTS

| | | | | |
|---|---|---|---|---|
| 5,440,385 A | * | 8/1995 | Fein et al. ................ | 356/239.1 |
| 5,495,337 A | * | 2/1996 | Goshorn et al. ............ | 356/601 |
| 6,122,048 A | * | 9/2000 | Cochran et al. .......... | 356/239.4 |
| 6,177,682 B1 | * | 1/2001 | Bartulovic et al. ..... | 250/559.44 |
| 6,522,777 B1 | * | 2/2003 | Paulsen et al. ............. | 382/154 |
| 6,552,783 B1 | * | 4/2003 | Schmidt et al. .......... | 356/237.4 |
| 6,621,566 B1 | * | 9/2003 | Aldrich et al. ........... | 356/237.1 |

FOREIGN PATENT DOCUMENTS

| | | |
|---|---|---|
| EP | 1 098 190 | 5/2001 |
| WO | WO 01/88592 | 11/2001 |

* cited by examiner

Primary Examiner—Michael P. Stafira
(74) Attorney, Agent, or Firm—Sughrue Mion, PLLC

(57) ABSTRACT

An inspection illuminates a generally specular surface of an electrical circuit with flashes of light. The flashed light comes form at least two spectrally different sources, and is temporally spaced. A camera forms an optical image of the circuit for each flash of light. Optical images are combined to provide a combined image. An analysis of the combined image can detect defects, and production related decisions may be based on this analysis.

43 Claims, 3 Drawing Sheets

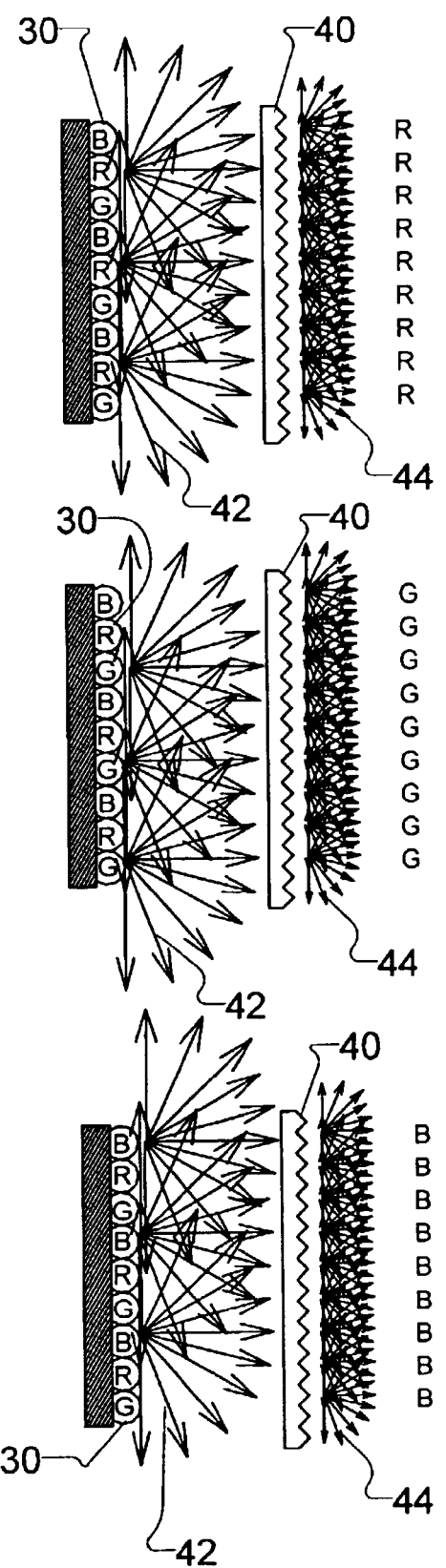

ILLUMINATION AND IMAGE ACQUISITION SYSTEM

FIELD OF THE INVENTION

The present invention relates generally to illumination and image acquisition systems and particularly to a color flash image acquisition assembly that is suitable for electrical circuit inspection, including the inspection of in-fabrication flat panel displays.

BACKGROUND OF THE INVENTION

Automated optical inspection (AOI) systems are typically employed in the inspection of electrical circuits, including printed circuit boards, flat panel displays, chip carriers, integrated circuits and the like. Commercially available AOI systems include the Inspire™ 9060, SK-75™ and V-300™ systems for inspecting bare printed circuit boards, the Trion™ system for inspecting populated printed circuit boards, FPI-6090™ and FPI-7590™ systems for inspecting flat display panels, and ICP 8060™ system for inspecting chip carriers. All of the above systems are commercially available from Orbotech Ltd. of Yavne, Israel.

A system for acquiring color images using color flashes in combination with a black and white camera is described in European Patent Application 1,098,190 A2, to Orbotech—Schuh, GMbH & Co., KG, published on May 9, 2001, the disclosure of which is incorporated herein by reference.

SUMMARY OF THE INVENTION

The present invention seeks to provide an improved system for acquiring color images of surfaces. A typical application for images acquired using a system configured and operative in accordance with the invention is for inspecting electrical circuits, particularly flat panel displays, for defects.

In accordance with a general aspect of the invention, an improved system is provided for acquiring color images. The improved system is particularly useful for acquiring brightfield color images of specular surfaces, such as portions of in-fabrication flat panel displays. The invention may be employed wherever it is desired to acquire a brightfield color image in which each of the component images, for example red, green and blue components, are in very precise and accurate alignment.

In accordance with an embodiment of the invention, the improved system comprises a sensor imaging a portion of a generally specular surface, and an illuminator providing at least two spectrally different and temporally separated flashes of light. The sensor and illuminator are arranged such that light from each flash of light output is incident on the portion of the specular surface generally at the same angle of incidence, and such that the sensor images a reflection of light reflected by the portion of the specular surface incident thereon. An image combiner is provided to combine images acquired with illumination from different flashes of light to produce a combined image.

Embodiments of the present invention may include one or more of the features which follow:

The illuminator includes a set of flash lights, and each of the flash lights emits light of a different color.

The set of flash lights comprises two or more flash lights, selected from a red flash light, a green flash light and a blue flash light.

The flash lights emit light within a given spectral range. The spectral ranges of the respective flash lights may be either overlapping or not overlapping.

The flash lights are LED emitters.

The LED emitters emitting red flash light, green flash light and blue flash light are mutually set apart from each other.

The LED emitters emitting red flash light, green flash light and blue flash light are mutually interlaced.

A light homogenizer is disposed between the illuminator and the surface. The light homogenizer treats light emitted by the LED emitters to appear as if emitted by an extended light source.

An at least partially reflective surface is disposed between the illuminator and an illuminated portion. The reflective surface reflects light from the illuminator to impinge on the portion generally along an axis normal thereto.

The reflective surface disposed between illuminator and the illuminated portion is configured as a beam splitter so as to transmit light emitted by the illuminator and reflected by the surface to impinge on the sensor.

The sensor is also disposed along an axis that is normal to the illuminated portion.

The illuminator and the sensor are configured and arranged such that an optical image of the imaged portion is a bright field image.

The generally specular surface being imaged is a surface of an in-fabrication electrical circuit, which is, for example, an in-fabrication display panel.

The system further comprises a defect detector operative to receive a combined image and to detect defects in the substrate in response to analyzing the combined image.

In accordance with another general aspect of the invention, the improved system is employed as part of a process for manufacturing electrical circuit substrates, such as flat panel displays. The process includes: forming a pattern on a generally specular substrate; illuminating a portion of a surface of the substrate with at least two spectrally different and temporally spaced flashes of light, each flash of light being incident on the surface at generally the same angles of incidence; acquiring at least a first optical image of the portion with a camera arranged to receive light from a first flash reflected by the portion of the generally specular surface; acquiring at least a second optical image of the portion with the camera arranged to receive light from a second flash reflected by the portion of the generally specular surface; combining the first optical image and the second optical image to form an inspection image; inspecting the inspection image for defects; and in response to the inspecting, performing a post inspection operation on the substrate. The post inspection operation includes at least one of the following: discarding the substrate, repairing the substrate or confirming that the substrate is not defective.

BRIEF DESCRIPTION OF THE DRAWINGS

The drawing figures depict, in highly simplified schematic form, embodiments reflecting the principles of the invention. Many items and details that will be readily understood by one familiar with this field have been omitted so as to avoid obscuring the invention. In the drawings:

FIGS. 2A–2C are simplified side view illustrations showing the operation of an illuminator employed in the system of FIG. 1A.

DETAILED DESCRIPTION OF A PREFERRED EMBODIMENT

The invention will now be taught using various exemplary embodiments. Although the embodiments are described in detail, it will be appreciated that the invention is not limited just to these embodiments, but has a scope that is significantly broader. The appended claims should be consulted to determine the full scope of the invention.

Figure 1A:
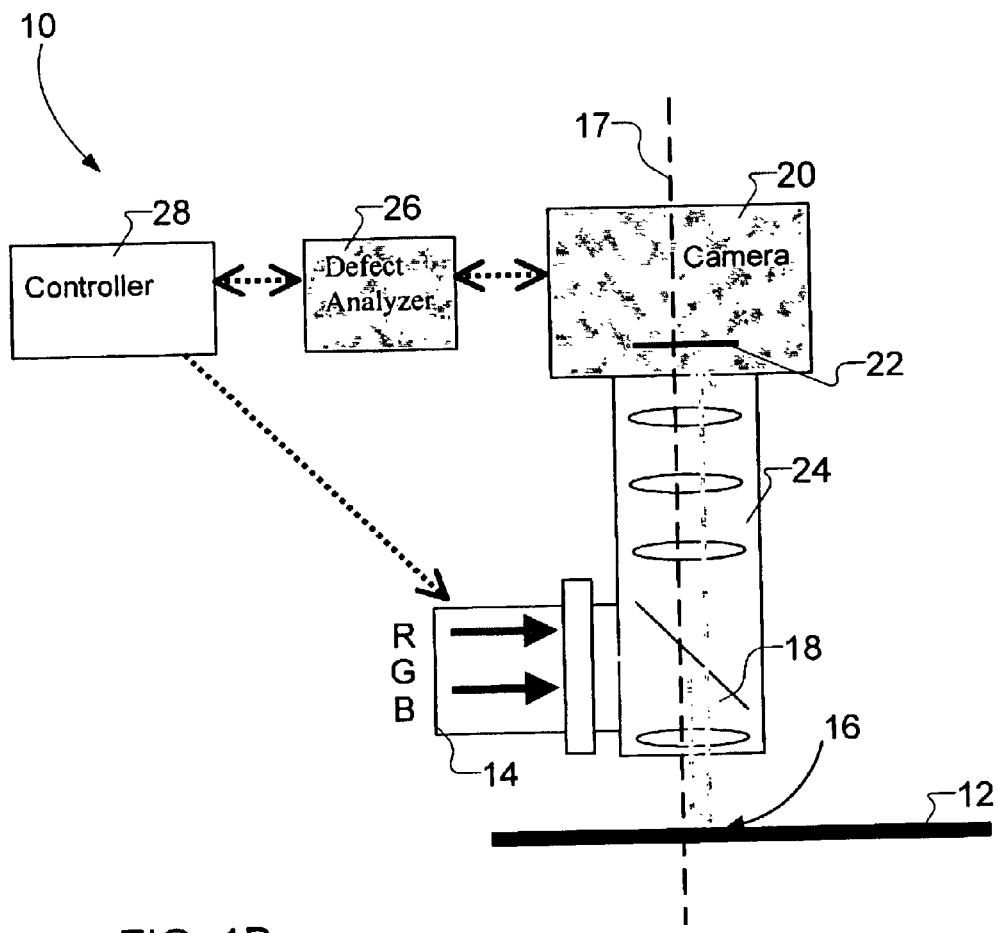
FIG. 1A is a simplified schematic diagram of an illumination and image acquisition system constructed and operative in accordance with an embodiment of the present invention.

Reference is now made to FIG. 1A which is a simplified schematic diagram of an illumination and image acquisition system 10 constructed and operative in accordance with an embodiment of the present invention.

System 10 is particularly suited for inspecting electrical circuits during the fabrication thereof. By way of amplification, and not limitation, as used herein the term electrical circuit should be understood to include in-fabrication flat panel displays, printed circuit boards before, during and after the assembly of integrated circuits thereon, integrated circuits, chip carriers and the like, as well as portions of the same. Electrical circuits may also include, for example, pixel arrays disposed on glass panels, and layers of dielectric substrate and electrical connectors that are combined together to form printed circuit boards.

In accordance with an embodiment of the present invention, an illumination and image acquisition system 10 is operative to acquire images of a surface of a substrate 12, such as a glass panel employed in the fabrication of a flat panel display or other suitable electrical circuit. System 10 typically is part of a defect inspection system (not shown), that is employed to detect defects in electrical circuits, such as in-fabrication flat panel displays during fabrication.

It is appreciated that surfaces of some electrical circuits, for example in-fabrication flat panel displays, are generally specular in nature. In accordance with an embodiment of the invention, the configuration of system 10 is optimized to inspect electrical circuits having specular surfaces for defects. The results of such inspection may be used, for example, for the purposes of discarding or repairing defective substrates 12, confirming that no defects are present on substrate 12, or to improve manufacturing processes employed during fabrication of electrical circuits.

As seen in FIG. 1A, system 10 generally includes an illuminator 14, illuminating a portion 16 of a surface to be imaged on substrate 12, a beam splitter 18 receiving light from illuminator 14 and directing the light to illuminate portion 16 of substrate 12. Moreover, as seen in FIG. 1A, in system 10 illuminator 14 illuminates portion 16 along an optical axis 17 which is generally normal to the surface of portion 16, and a camera 20, comprising a sensor 22, such as a CCD or CMOS type sensor, is arranged to acquire an optical image of portion 16.

In the arrangement seen in FIG. 1A, camera 20 receives light provided by illuminator 14 which is reflected by portion 16 and which passes through beam splitter 18 and imaging optics 24, all of which are disposed generally along optical axis 17. Consequently, in accordance with an embodiment of the invention, as shown in FIG. 1A, the angles of illumination output by illuminator 14 are such that the images acquired by camera 20 are bright field images. Optionally, illuminator 14 may be configured to provide illumination which results in the acquisition of darkfield images by camera 20.

It is a feature of an embodiment of the present invention that illuminator 14 provides at least two spectrally different and temporally spaced flashes of light. The respective spectra of the flashes of light may be overlapping or non-overlapping spectra. The different spectra are indicated in FIG. 1A by the arrows labeled R, G and B respectively. In accordance with an embodiment of the invention, illumination in each of the different spectra is provided by illuminator 14 as a sequence of time separated flashes, which are neither emitted at the same time nor at overlapping times.

Moreover, in accordance with an embodiment of the invention, illuminator 14 is configured such that each flash of light is incident on a portion 16 of the surface at generally the same angles of incidence. This enables each image acquired by camera 20 to be acquired under generally uniform and controlled conditions, notwithstanding a change in spectra between subsequent flashes.

In accordance with an embodiment of the invention, a composite image is formed of sequentially acquired images that are each illuminated by light in a different spectral range. The sequential illumination with a different color produces images which correspond to a color separation. Provided that the relative locations of illuminator 14, camera 20 and portion 16 are held steady while each of the images is acquired, then each of the different color images can be overlayed in highly precise and accurate alignment. Thus, when suitably color balanced illumination is employed to sequentially illuminate portion 16, the combination of resulting images reconstructs a color image of portion 16.

As seen in FIG. 1A, a frame grabber 26 is provided to capture images acquired by camera 20. Additionally a controller 28 is provided to coordinate the providing of light flashes by illuminator 14, and the capturing of images by camera 20 and frame grabber 26. The resulting images may be provided to a defect detector (not shown) for image inspection and analysis as known in the art.

Figure 1B:
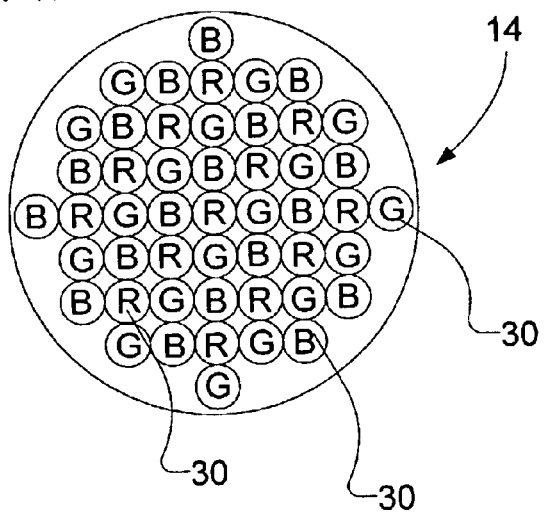
FIG. 1B is a simplified front view illustration of an illuminator employed in the system of FIG. 1A.

Reference is now made to FIG. 1B which is a simplified front view illustration of illuminator 14 employed in system 10 seen in FIG. 1A, and to FIGS. 2A–2C which are simplified side view illustrations showing operation of illuminator 14 in accordance with an embodiment of the invention.

In accordance with an embodiment of the invention, illuminator 14 comprises at least two sets, and preferably a multiplicity, of flash lights 30 each set of which emits light in a different spectral range to selectably provide different color light. For example some of flash lights 30, designated R, emit red light. Some of flash lights 30, designated G, emit green light. Some of flash lights 30, designated B, emit blue light.

Means for providing different color light are well known in the art. For example, flash lights 30 may be light emitting diodes emitting light in a well defined spectral range. Alternatively, flash 30 lights may comprise flash tubes, for example xenon flash tubes, emitting broad spectrum light, that is to say generally white light, in combination with suitable optical filters (not shown). Any other suitable means for providing spectrally different and temporally separated flashes of light may be employed.

In accordance with an embodiment of the invention, as seen for example in FIG. 1B, flash lights 30 are mutually spaced apart one from the other. Moreover, the flash lights 30 of different colors are arranged in an interlaced pattern. Various patterns of interlacing may be employed, it being desirable, in accordance with an embodiment of the invention, to configure illuminator 14 such that portion 16 is generally uniformly illuminated, and such that illumination is provided at generally the same angles of incidence, regardless of the color of the illumination. Various lenses (not shown) may be disposed between illuminator 14 and portion 16 in order to provide a suitable angular extent of illumination incident on portion 16, and to suitably adjust the spatial extent of illumination incident on portion 16.

In accordance with an embodiment of the invention, a light homogenizer 40 (see FIGS. 2A–2C), for example a glass rod in combination with a diffuser although other suitable light homogenizing optical elements may be used, is also provided in order to further homogenize light emitted by flash lights 30 and to ensure that the intensity of illumination provided by illuminator 14 is spatially uniform, regardless of whatever color light is provided, or whichever flash lights 30 emit the illumination. It is noted that the configuration of light homogenizer 40 is a highly generalized and simplified schematic representation of a light homogenizer, and that the actual configuration of a light homogenizer is likely to differ from that shown. Thus, as seen in each of FIGS. 2A–2C, only some of flash lights 30 are used to generate red, green or blue light respectively.

The use of spaced apart flash lights has the potential to produce illumination which is not spatially uniform for each color, or illumination in which spatial non-uniformity differs among the colors. The relative non-uniformity is indicated by relatively large gaps between respective pre-homogenization arrows 42 in FIGS. 2A–2C. After light passes through homogenizer 40, illumination having a significantly higher degree of spatially uniformity is produced for illumination in each of the respective colors. The relative uniformity is indicated by relatively small gaps between respective post-homogenization arrows 44 in FIGS. 2A–2C.

Figure 3:
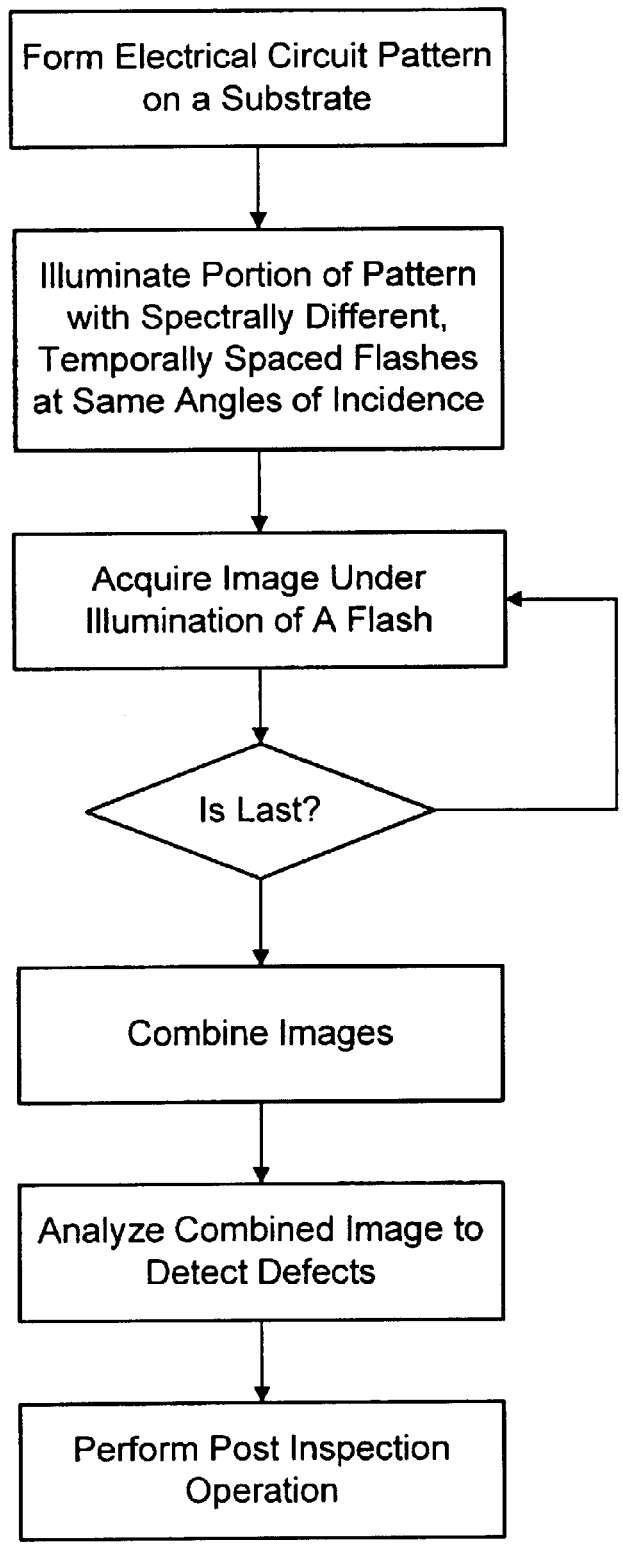
FIG. 3 which is a simplified flow diagram of a method for manufacturing electrical circuits in accordance with an embodiment of the invention.

Reference is now made to FIG. 3 which is a flow diagram of a methodology 100 for manufacturing electrical circuits. Methodology 100, which employs an inspection system such as system 10 (FIG. 1) is particularly suited for manufacturing electrical circuits formed on generally specular substrates.

Method 100 commences with the operation of forming at least a portion of an electrical circuit on a substrate. For example, in the manufacture of flat panel displays, an array of pixels is formed on a glass substrate.

Subsequently, a portion of the electrical circuit to be inspected is illuminated with at least two spectrally different and temporally spaced flashes of light. It is a feature of an embodiment of the present invention that each flash of light is incident on the substrate at generally the same angles of incidence.

A first optical image of the portion is acquired, for example by camera 20 (FIG. 1) during a time interval in which said surface is illuminated by a first flash of light. Subsequently, a second optical image of the same portion is acquired during a time interval in which the surface is illuminated by a second flash of light. Although a second flash of light, as noted above, is spectrally different from the first flash of light, both are incident on the substrate at generally the same angles of incidence. It is appreciated that additional images may be acquired under the illumination of additional flashes of light, each provided in a different spectrum but so as to impinge on the substrate at generally the same angles of incidence.

The first optical image and the second optical image are combined to form a combined image. The combined image is, for example, a color image, and each of the first and second optical images comprise, respectively, color components of the combined color image.

In a subsequent operation, the combined image is analyzed to detect defects in the substrate, or in a portion of a pattern formed on the substrate. Then, in response to analysis of the combined image, a post inspection operation is performed. The post inspection operation may be, for example one or more of the following operations: discarding a substrate which is found to be defective or which has a defective pattern formed thereon; repairing a portion in which a defect has been detected; confirming that a substrate, or a pattern portion formed thereon, is not defective; or modifying a manufacturing process that is employed to form a pattern portion on the substrate.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. An inspection system comprising:
an illuminator illuminating a portion of a pattern formed on a generally specular surface to be imaged, said illuminator providing at least two spectrally different and temporally spaced flashes of light, each flash of light being incident on said portion at generally the same angles of incidence;
a camera arranged to receive light from said flashes and reflected by said portion of said generally specular surface to acquire at least one optical image of said portion per flash; and
an image combiner operative to combine images acquired from different flashes to produce a combined image.

2. The inspection system claimed in claim 1 and further comprising a defect analyzer operative to receive and analyze the combined image to detect defects in said pattern.

3. The inspection system claimed in claim 1 and wherein the spectrum of light of each of said different flashes is non-overlapping.

4. The inspection system claimed in claim 1 and wherein the spectrum of light of each of said different flashes is partially overlapping.

5. The inspection system claimed in claim 1 and wherein said illuminator comprises at least two flash lights, each flash light emitting light of a different color.

6. The inspection system claimed in claim 5 and wherein said at least two flash lights comprise a red flash light, a green flash light and a blue flash light.

7. The inspection system claimed in claim 5 and wherein said at least two flash lights comprise LED emitters.

8. The inspection system claimed in claim 6 and wherein said at least two flash lights comprise LED emitters.

9. The inspection system claimed in claim 8 and wherein LED emitters emitting said red flash light, LED emitters emitting said green flash light and LED emitters emitting said blue flash light are mutually set apart.

10. The inspection system claimed in claim 9 and wherein said LED emitters emitting said red flash light, LED emitters emitting said green flash light and LED emitters emitting said blue flash light comprise a plurality of mutually interlaced LED emitters.

11. The inspection system claimed in claim 10 and further comprising a light homogenizer disposed between said illuminator and said surface.

12. The inspection system claimed in claim 11 and wherein said light homogenizer is operative to treat light emitted by said LED emitters such that such light appears as if emitted by an extended light source.

13. The inspection system claimed in claim 1 and further comprising an at least partially reflective surface interposed between said illuminator and said portion, said at least partially reflective surface reflecting light from said illuminator to impinge on said portion generally along an axis normal to said portion.

14. The inspection system claimed in claim 13 and wherein said at least partially reflective surface is disposed along said normal axis, and is configured to transmit light reflected by said surface to impinge on said camera.

15. The inspection system claimed in claim 13 and wherein said camera is disposed along said normal axis.

16. The inspection system claimed in claim 1 and wherein said optical image comprises a bright field image of said portion.

17. The inspection system claimed in claim 1 and wherein said generally specular surface is a surface of an in-fabrication electrical circuit.

18. The inspection system claimed in claim 17 and wherein said in-fabrication electrical circuit comprises an in-fabrication display panel.

19. An imager comprising:
    an illuminator illuminating a portion of a generally specular surface to be imaged, said illuminator providing at least two spectrally different and temporally spaced flashes of light, each flash of light being incident on said surface at generally the same angles of incidence;
    a camera arranged to receive light from said flashes and reflected by said portion of said generally specular surface to acquire at least one optical image of said portion per flash; and
    an image combiner operative to combine images acquired from different flashes to produce a combined image.

20. The imager claimed in claim 19 and wherein the spectrum of light of each of said different flashes is non-overlapping.

21. The imager claimed in claim 19 and wherein the spectrum of light of each of said different flashes is partially overlapping.

22. The imager claimed in claim 19 and wherein said illuminator comprises at least two flash lights, each flash light emitting light of a different color.

23. The imager claimed in claim 22 and wherein said at least two flash lights comprise a red flash light, a green flash light and a blue flash light.

24. The imager claimed in claim 22 and wherein said at least two flash lights comprise LED emitters.

25. The imager claimed in claim 23 and wherein said at least two flash lights comprise LED emitters.

26. The imager claimed in claim 25 and wherein LED emitters emitting said red flash light, LED emitters emitting said green flash light and LED emitters emitting said blue flash light are mutually set apart.

27. The imager claimed in claim 26 and wherein said LED emitters emitting said red flash light, LED emitters emitting said green flash light and LED emitters emitting said blue flash light comprise a plurality of mutually interlaced LED emitters.

28. The imager claimed in claim 27 and further comprising a light homogenizer disposed between said illuminator and said surface.

29. The imager claimed in claim 28 and wherein said light homogenizer is operative to treat light emitted by said LED emitters such that such light appears as if emitted by an extended light source.

30. The imager claimed in claim 19 and further comprising an at least partially reflective surface interposed between said illuminator and said portion, said at least partially reflective surface reflecting light from said illuminator to impinge on said portion generally along an axis normal to said portion.

31. The imager claimed in claim 30 and wherein said at least partially reflective surface is disposed along said normal axis, and is configured to transmit light reflected by said surface to impinge on said camera.

32. The imager claimed in claim 30 and wherein said camera is disposed along said normal axis.

33. The imager claimed in claim 19 and wherein said illuminator optical image comprises a bright field image of said portion.

34. The imager claimed in claim 19 and wherein said generally specular surface is a surface of an in-fabrication electrical circuit.

35. The imager claimed in claim 34 and wherein said in-fabrication electrical circuit comprises an in-fabrication display panel.

36. The imager claimed in claim 19 and further comprising a defect analyzer operative to receive and analyze a combined image to detect defects in said surface.

37. A method for inspecting surfaces for defects, comprising:
    illuminating a portion of a generally specular surface to be inspected with at least two spectrally different and temporally spaced flashes of light, each flash of light being incident on said surface at generally the same angles of incidence;
    acquiring a first optical image of said portion of said surface illuminated by a first flash among said at least two spectrally different and temporally spaced flashes;
    acquiring a second optical image of said portion of said surface being illuminated by a second flash among said at least two spectrally different and temporally spaced flashes; and
    combining said first optical image and said second optical image to generate a combined image.

38. The method claimed in claim 37 and further comprising analyzing said combined image to detect defects in said substrate.

39. A method for fabricating electrical circuit, comprising:
    forming at least a portion of an electrical circuit on a substrate;
    illuminating said portion with at least two spectrally different and temporally spaced flashes of light, each flash of light being incident on said substrate at generally the same angles of incidence;
    acquiring a first optical image of said portion during a time interval in which said surface is illuminated by a first flash among said at least two spectrally different and temporally spaced flashes;
    acquiring a second optical image of said portion during a time interval in which said surface is illuminated by a second flash among said at least two spectrally different and temporally spaced flashes;
    combining said first optical image and said second optical image to form a combined image;
    inspecting said combined image; and
    in response to said inspecting, performing a post inspection operation.

40. The method of claim 39 and wherein said post inspection operation comprises discarding said substrate.

41. The method of claim 39 and wherein said post inspection operation comprises repairing said portion.

42. The method of claim 39 and wherein said post inspection operation comprises confirming that said portion is not defective.

43. The method of claim 39 and wherein said post inspection operation comprises modifying a manufacturing process employed to form said portion.

* * * * *